United States Patent [19]

Hottinger et al.

[11] Patent Number: 5,412,086
[45] Date of Patent: May 2, 1995

[54] DNA PROBE FOR LACTOBACILLUS HELVETICUS

[75] Inventors: Herbert Hottinger, Blonay; Beat Mollet, Mollie-Margot; Nathalie Pilloud, Tour-de-Peilz, all of Switzerland

[73] Assignee: Nestec S.A., Vevey, Switzerland

[21] Appl. No.: 892,403

[22] Filed: May 28, 1992

Related U.S. Application Data

[63] Continuation of Ser. No. 494,138, Mar. 14, 1990, abandoned.

[30] Foreign Application Priority Data

Feb. 10, 1990 [EP] European Pat. Off. ............ 90102650

[51] Int. Cl.$^6$ ............ C07H 21/04; C12Q 1/68; C12N 15/00
[52] U.S. Cl. ............ 536/24.32; 435/6; 935/77; 935/78
[58] Field of Search ............ 435/6; 536/27, 24.32; 935/77, 78

[56] References Cited

PUBLICATIONS

Bergey's Manual of Systematic Bacteriology, v. 2, 1986, p. 1224, Williams & Wilkins.
Takiguchi et al, Applied and Env. Microbiol., Jun. 1989, vol. 55, No. 6, pp. 1653–1655.
Mariatis et al, Molecular Cloning & Laboratory Manual, Cold Spring Harbor Laboratory, 1982, p. 117.
Petrick et al, Applied Env. Microbiology, 54, pp. 405–408, 1988.
Nathalie Pilloud, et al., "DNA Probes for the Detection of *Lactobacillus helveticus*", System Appl. Microbiol. vol. 13, pp. 345–349, 1990.
M. C. Zwahlen, et al. "Nucleotide sequence of a *Lactobacillus delbrueckii* gene encoding a minor (UCG) tRNAser." Nucleic Acids Research, vol. 17, No. 4, (1989) p. 1772.
H. Hottinger, et al. "Allele-specific complementation of an *Escherichia coli* leuβ metation by a *Lactobacillus bulagricus* tRNA gene." Gene, vol. 60, pp. 75≧83 (1987).
Chemical Abstracts, No. 100:115815v (1984).
G. Tannock, et al., "Biotin–Labeled Plasmid DNA Probes for Detection of Epithelium–Associated Strains of Lactobacilli." Appl. Environ. Microbiol., vol. 55, No. 2, pp. 461–464 (1989).
J. Jagow, et al., "Enumeration by DNA Colony in Artificially Contaminated Food." Appl. Environ. Microbiol., vol. 51, No. 2, pp. 441–443 (1986).
R. H. Barker, Jr., et al., "Specific DNA Probe for the Diagnosis of Plasmodium falciparum Malaria". Science 231, 1434–1436 (1986).
F. A. Rubin, et al., Development of a DNA Probe to Detect Salmonella typhi. J. Clin. Microbiol. vol. 22, No. 4, 600–605 (1985).
J. Kraus, et al. "A cloned 23S rRNA gene fragment of Bacillus subtilis and its use as a hybridization probe of conserved character." FEMS Microbiol. Lett. 33 89–93 (1986).
F. Malouin, et al., "DNA Probe Technology for Rapid Detection of *Haemophilus influenzae* in Clinical Specimens." J. Clin. Microbiol. vol. 26, No. 10, 2132–2138 (1988).
J. Brandsma, et al. "Nucleic acid spot hybridization: Rapid quantitative screening of lymphoid cell lines for Epstein–Barr viral DNA." Proc. Natl. Acad. Sci. USA, vol. 77, No. 11, 6851–6855 (1980).
P. Stålhandske, et al., "Identification of DNA Viruses by Membrane filter Hybridization". J. Clin. Microbiol. vol. 15, No. 4, 744–747 (1982).

(List continued on next page.)

*Primary Examiner*—Mindy B. Fleisher
*Attorney, Agent, or Firm*—Vogt & O'Donnell

[57] ABSTRACT

Strains of the *Lactobacillus helveticus* species are identified by a probe having a DNA fragment which hybridizes specifically to DNA of strains of the *L. helveticus* species.

8 Claims, 2 Drawing Sheets

PUBLICATIONS

P. Stålhandske, et al., "Detection of Adenoviruses in Stool Specimens by Nucleic Acid spot Hybridization". J. Med. Virol. 16, 213–218 (1985).

J. Flores, et al. "A Dot Hybridisation Assay for Detection of Rotavirus". The Lancet, 555–559 (1983).

M. Lin, et al. "Diagnosis of Rotavirus Infection with Cloned cDNA Copies of Viral Genome Segments." J. Virol. vol. 55, No. 2, 509–512 (1985).

A. Chang, et al., "Construction and Characterization of Amplifiable Multicopy DNA Cloning Vehicles Derived from p. 15 A Cryptic Miniplasmid." J. of Bacteriol. vol. 134, No. 3, 1141–1156 (1978).

H. A. R. Petrick, et al., "Isolation of a DNA Probe for *Lactobacillus curvatus*." Appl. Environ. Microbiol. vol. 54, No. 2, 405–408 (1988).

E. M. Southern, "Detection of Specific Sequences Among DNA Fragments Separated by Gel Electrophoresis." J. Mol. Biol. 98, 503–517 (1975).

DNA PROBE FOR LACTOBACILLUS HELVETICUS

CROSS REFERENCE TO RELATED APPLICATION

This application is a continuing application of application Ser. No. 07/494,138, filed Mar. 14, 1990, now abandoned.

BACKGROUND OF THE INVENTION

The present invention relates to a DNA probe for identifying bacterial strains of the *Lactobacillus helveticus* species, a process for producing such a probe and a method for identifying bacterial strains of this species with this DNA probe.

*Lactobacillus helveticus* is a very important bacteria for the fermentation of food. It is predominantly used in the fermentation of milk products and is found in starter cultures for some cheese and, in some countries, also for yoghurt production. Fermentation and maturation of these food products usually result from growth association and interaction of different bacteria, in most cases different Lactobacilli, Lactococci and other bacterial species. As most of these bacterial species have very similar nutritional requirements and grow under similar environmental conditions, a clear identification within the Lactobacillus species is sometimes very difficult. In particular, it may be difficult to differentiate between the two yoghurt bacteria *L. bulgaricus*, which belongs to the species of *L. delbrueckii*, and *L. helveticus* (formerly also called *L. jugurti*; O. Kandler and N. Weiss, Bergey's Manual of Systematic Bacteriology, vol. 2, 1208–1260, 1986). So far the classification of all these species is tedious and involves unreliable criteria, like sugar fermentation patterns and acid production. Due to these tests an identification of these different species remains doubtful and often arbitrary.

DNA hybridisation techniques, using specific DNA probes, are a very valuable tool for the identification of bacterial and viral strains, and have already found application in clinical diagnostics. Such DNA probes have already been used for the identification of *Yersinia enterocolitica* (J. Jagow et al., Appl. Environ. Microbiol. 51, 441–443, 1986), *Plasmodium falciparum* (R. H. Barker et al., Science 231, 1434–1436, 1986), *Salmonella typhi* (F. A. Rubin et al., J. Clin. Microbiol. 22, 600–605, 1985), *Bacillus subtilis* (J. Krauss et al., FEMS Microbiol. Lett. 33, 89–93, 1986), *Haemophilus influenzae* (F. Malouin et al., J. Clin. Microbiol. 26, 2132–2138, 1988) and other bacterial species, of DNA viruses (J. Brandsma et al., Proc. Natl. Acad. Sci. USA, 77, 6851–6855; P. Stolhandske et al., J. Clin. Microbiol. 15, 744–747, 1982; P. Stolhandske et al., J. Med. Virol. 12, 213–218, 1985), as well as RNA viruses (J. Flores et al., Lanceti, 555–559, 1983; M. Lin et al., J. Virol. 55, 509–512, 1985).

In the species of Lactobacillus, DNA probes for *L. curvatus* (H. A. R. Petrick et al., Appl. Environ. Microbiol. 54, 405–408, 1988,) which is specifically associated with spoilage of vacuum-packed meat, and for the *L. delbrueckii* species, comprising *L. bulgaricus*, *L. lactis* and *L. delbrueckii* (M. Delley et al., submitted), have been isolated. It would be of use in the dairy industry not only to be able to quickly identify *L. delbrueckii*, as can be done by the procedure described in our European Patent Application No. 89106016.2, but also to have a quick and reliable method to detect and classify strains belonging to the *L. helveticus* species.

SUMMARY OF THE INVENTION

Accordingly, a first object of the present invention is to provide a specific DNA probe, which can be used in hybridisation procedures to specifically identify strains belonging to the *Lactobacillus helveticus* species, either in bacterial cultures, or as food constituents or during food processing, e.g. during industrial fermentation.

A second object of the present invention is to provide a process for producing such a specific DNA probe.

A third object of the present invention is to provide a method for specifically identifying strains belonging to the *L. helveticus* species with this DNA probe.

To this end, firstly, the DNA probe according to the present invention comprises a DNA fragment which hybridizes specifically to DNA of strains of the *L. helveticus* species under stringent conditions. This DNA fragment is preferably labeled by any suitable means, such as $^{32}P$, $^{35}S$ or biotin, for example. Preferably, this DNA fragment comprises a HindIII fragment of DNA from a strain of the *L. helveticus* species.

Secondly, the process for producing a DNA probe according to the present invention comprises preparing a HindIII clonebank from a strain of the *L. helveticus* species and isolating therefrom a clone of which a HindIII DNA fragment is capable of hybridisation to DNA of strains of the *L. helveticus* species.

Thirdly, the method for identifying a bacterial strain of the *L. helveticus* species according to the present invention comprises preparing DNA of a strain to be identified and checking whether this DNA hybridises to the present probe or to a probe produced by the present process. In a preferred embodiment of this method, the DNA is prepared by growing cells of the strain to be identified on a culture medium supplemented with a fermentable carbon source, incubating them in the presence of proteinases, treating them with an N-acetyl-muramidase, further incubating them in the presence of an emulsifying agent, a chelating agent and a proteinase, phenol extracting DNA therefrom, ethanol precipitating the extracted DNA, treating this DNA with an RNase and chloroform extracting the RNase treated DNA.

DEPOSIT OF BIOLOGICAL MATERIALS

The fragments sLH1 and sLH2 were deposited pursuant to the Budapest Treaty on December 14, 1994, in the Collection Nationale de Cultures de Microorganismes (CNCM), Institut Pasteur, 25 rue du Dr. Roux, 75724 Paris Cédex 15, France, where they were given the numbers CNCM I-1505 (sLH1) and I-1506 (sLH2).—

Enzymes which do not cut within this fragment are:
ApaI, AvaI, BamHI, BglI, BglII, BstBI, CfoI, EcoRI, Hae II, HindIII, KpnI, MluI, NarI, NcoI, NdeI, NheI, NotI, NruI, NsiI, PstI, PvuI, SacI, SacII, SalI, SmaI, SnaBI, SphI, SspI and StuI.

Figure 2:
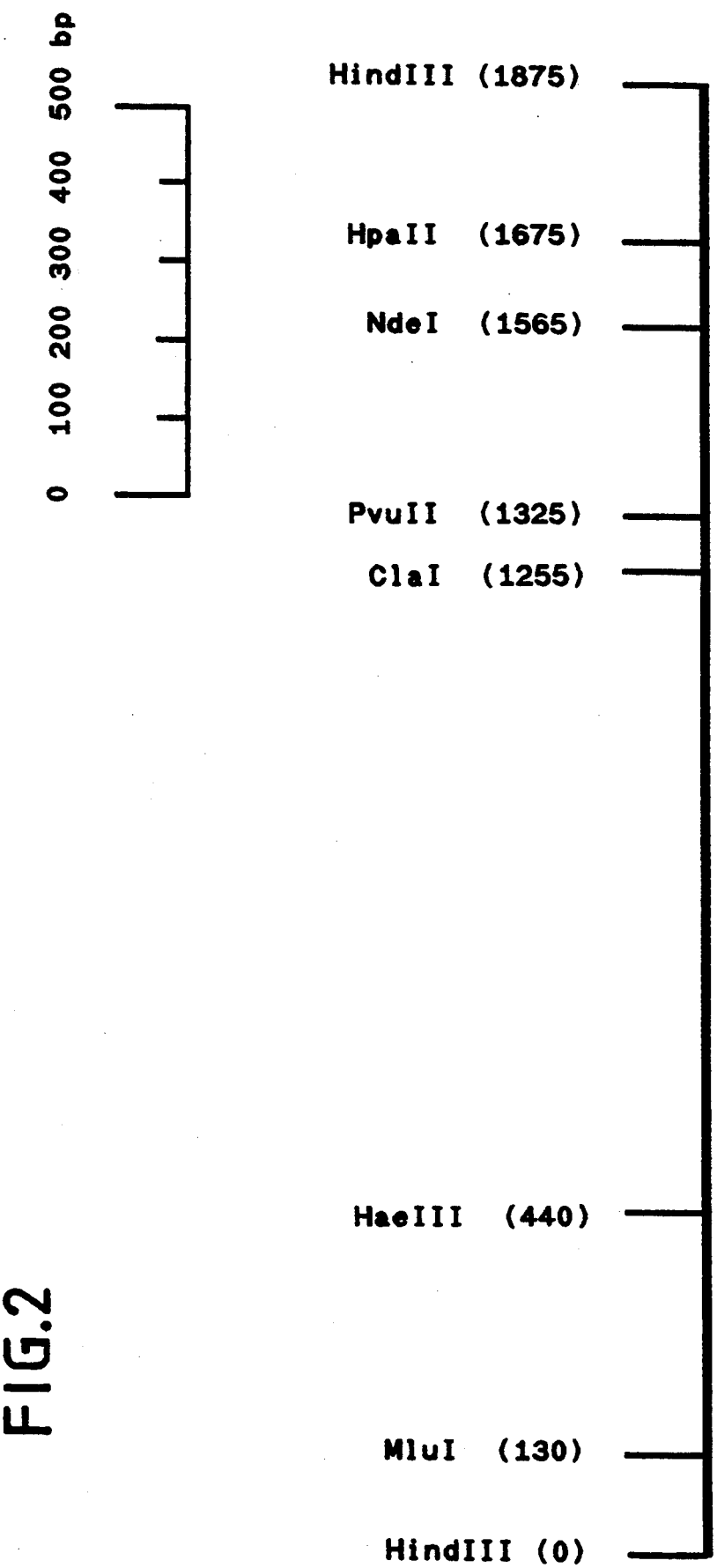

FIG. 2 is a restriction map of another cloned HindIII DNA fragment, sLH2, originating from *L. helveticus* ATCC 15009 and being about 1875 base pair long.

Enzymes which do not cut this fragment are:
AccI, AflII, AvaI, BalI, BglI, BglII, DraI, EcoRV, KpnI, NarI, NcoI, NheI, NotI, NruI, NsiI, PstI, PvuI, SacI, SacII, SalI, ScaI, SmaI, SphI, SspI and StuI.

Figure 1:
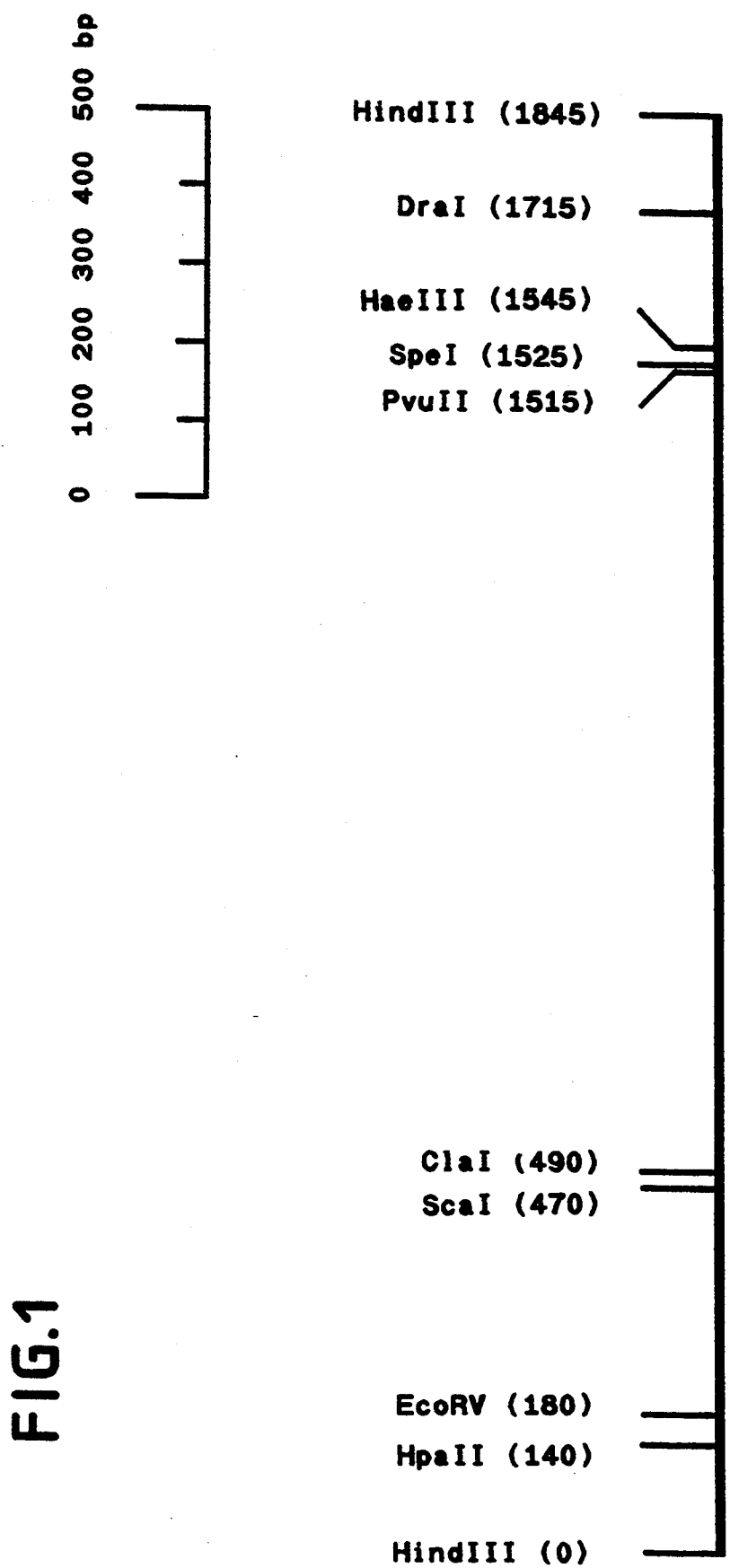
FIG. 1 is a restriction map of a cloned HindIII DNA fragment, sLH1, originating from *L. helveticus* ATCC 15009 and being about 1845 base pair long.

In FIGS. 1 and 2, the numbers in brackets indicate the relative position of the appropriate restriction sites in base pairs.

DETAILED DESCRIPTION OF THE INVENTION

In order to obtain DNA probes which specifically identify strains belonging to the species of L. helveticus, it was possible to randomly clone HindIII DNA fragments originating from L. helveticus strains and to screen them for species specific hybridisation.

The preferred vector for transforming a clone bank of HindIII DNA fragments of L. helveticus was the plasmid pACYC184, which is capable of being transformed into an E. coli strain, e.g. in the preferred E. coli strain HB101.

Especially specific probes were made of HindIII DNA fragments originating from strain L. helveticus ATCC 15009, e.g. from two DNA fragments sLH1 and sLH2.

In addition to the above mentioned preferred way of preparing DNA of a strain to be identified, it was also possible to prepare this DNA by simply lysing cells of this strain, either from cultures or on solid supports such as e.g. filter paper or nitrocellulose paper, and to sucessfully carry out identification tests on this DNA with the probes of the present invention.

In screening experiments applying dotblot hybridisation, over 50 different Lactobacillus strains from different origins were tested. It could be shown that probes according to the present invention only hybridised specifically to the L. helveticus species, and that they had a very high sensitivity.

MATERIALS AND METHODS

Bacteria and Plasmid

Lactic acid bacteria used in the Example hereafter are shown on table I. The E. coli strain is HB101 (leuB6 proA2 recA13 thi1 ara14 lacY1 galK2 xyl5 mtl1 rpsL20 supE44 hsdS20). The plasmid used as vector is pACYC184 (A. C. Y. Chang and S. N. Cohen, J. Bacteriol. 134:1141–1156, 1978).

Media

For growth of the different Lactobacilli, Lactococci and Propionibacteria MRS broth (Difco Laboratories) was used, supplemented with 1% lactose. E. coli strain was grown in LB medium.

Preparation of DNA i) DNA from Lactobacillus, Lactococcus and Propionibacteria Cells were diluted from overnight cultures into 10 ml MRS, supplemented with 1% lactose and grown to mid-log phase at 43° C. The cells were then harvested by centrifugation, washed once in cold 1M NaCl, and incubated for 1 h at 37° C. in the presence of Proteinase K (250 µg/ml) and Pronase E (500 µg/ml). The cells were washed in TE (10 mM Tris hydrochloride pH 7.4; 1 mM EDTA) and treated with Mutanolysin (200 µg/ml) in the presence of TE for 1 h at 37° C. SDS. EDTA and Proteinase K were added to a final concentration of 0.1%, 75 mM and 200 µg/ml, resp., and incubated for 4 h at 65° C. The DNA was then phenol extracted, ethanol precipitated and spooled onto a sterile toothpick. The DNA was resuspended in TE in the presence of RNase A (200 µg/ml), chloroform extracted, reprecipitated in ethanol and spooled again onto a toothpick. The DNA was then resuspended in 100 µl of TE and stored at 4° C.

ii) Plasmid DNA from E. coli

Plasmid DNA from E. coli was isolated and as needed purified on CsCl gradients according to Maniatis et al. (Molecular cloning: a laboratory manual. Cold Spring Harbor Laboratory, Cold Spring Harbor, N.Y. 1982). Chemicals were purchased from E. Merck Chemicals Inc. and the enzymes from Sigma Chemical Co.

Preparing a HindIII Clone Bank from a Strain of L. helveticus

DNA of L. helveticus ATCC 15009 was digested to completion with HindIII and ligated into vector pACYC184 which was linearised at its unique HindIII site and phosphatase treated. The ligation mixture was transformed into HB101, plated onto LB plates supplemented with 30 µg/ml chloramphenicol and grown at 37° C. overnight. Single colonies were grown in LB supplemented with chloramphenicol, their plasmids extracted, digested with HindIII and analysed by agarose gel electrophoresis. 90% of the analysed clones contained L. helveticus HindIII DNA fragments.

Labelling of DNA Fragments

To radioactively label the DNA we used a fill-in-replacement DNA synthesis or nick-translation reaction (Maniatis et al.). The Klenow fragment of DNA polymerase I and E. coli DNA polymerase I were purchased from Boehringer-Mannheim, [$\alpha$-$^{32}$P] dATP from Amersham Co.

Dotblot Hybridisation Procedures

Aliquots of 200 ng of chromosomal DNA in TE were denatured by heating for 5 min. at 95° C. SSC was added to the aliquots to give a final concentration of 16×SSC and then the mixture was spotted onto 10×SSC wetted GeneScreen paper and rinsed once with 20×SSC. A Bio-Rad dotblot apparatus was used. The filter was then ready for DNA hybridisation, applying standard procedures with hybridisation with 6×SSC at 65° C. and a subsequent wash with 0.1×SSC at 65° C. (E. Southern, J. Mol. Biol. 98, 503–517, 1975). As DNA probes we used either total plasmids or HindIII fragment DNA which was $^{32}$P labelled. To detect the hybridisation signals, the filters were used to expose X-ray films.

Restriction Mapping

Restriction enzymes were purchased from Boehringer-Mannheim Co. and New England Biolabs Co. and were used as recommended by the suppliers.

EXAMPLE

Isolation of L. helveticus DNA Probes

HindIII digested chromosomal DNA of L. helveticus ATCC 15009 has been used to prepare a clone bank as described above. Several clones were isolated and used as DNA probes in dotblot hybridisation experiments using filters containing DNA samples of a selected number of different lactic acid bacteria. The hybridisation results revealed that about 70% of the tested L. helveticus clones hybridised only to the different L. helveticus samples on the dotblot filters. The other 30% of the clones tested hybridised also to a variety of other unrelated species and genera of the lactic acid bacteria. For the following Examples, two DNA probes were selected which were very specific for the L. helveticus species. They are referred to as "sLH1" and "sLH2" in the present specification and claims.

Restriction Mapping of sLH1 and sLH2

A restriction map of the DNA fragments sLH1 and sLH2 was determined using several restriction enzymes. The results are shown in FIG. 1 and 2 (see brief description of the drawing here above).

Specificity and Sensitivity of the DNA Probes sLH1 and sLH2

The two DNA probes sLH1 and sLH2 were tested against many different representatives of the Lactobacillus genus and other lactic acid bacteria with dotblot hybridisations. For these hybridisation experiments, only the HindIII DNA fragments originating from *L. helveticus*, isolated from the plasmids, were used as DNA probes. The results of the dotblots showed that both DNA probes only hybridise to DNA derived from the bacterial species of *L. helveticus*. All other strains tested of different Lactobacillus species, of Lactococcus and Propionibacteria did not show any hybridisation. The only exceptions we observed, were two strains of *L. acidophilus*, N21 and N22, which gave a weak hybridisation signal with sLH1 and sLH2. However, these weak signals can clearly be differentiated from the much stronger hybridisation signals of strains belonging to the species of *L. helveticus*. The complete results are summarised in table I.

In order to test the sensitivity of our dotblots we made filters of serial dilutions of DNA from different Lactobacillus strains and used them for hybridisation with the probes sLH1 and sLH2. The results can be summarised as follows:

i. We easily could detect positive hybridisation signals with all the different strains of *L. helveticus* at DNA quantities as low as 2 ng per spot.

ii. All other bacterial strains tested as listed in table I do not show hybridisation signals at DNA quantities of 200 ng per spot.

iii. At DNA amount between 200 ng and 1.6 μg per spot many strains of the *L. acidophilus* species started to give rise to hybridisation signals.

iv. The following strains have been tested at DNA quantities of 1.6 μg per spot and did not show any hybridisation signals: *L. lactis* N4, *L. fermentum* N7, *L. plantarum* N24, *L. buchneri* N25, *L. brevis* N26, *L. casei* N27, *L. bulgaricus* N123, *L. maltaromicus* N207, *L. reuteri* N211 and *E. coli* HB101.

TABLE I

| Species | Bacterial strains Source | Strain[a] | sLH1[b] | sLH2[b] |
|---|---|---|---|---|
| L. helveticus | ATCC 15009 | N2 | + | + |
| L. lactis (type) | ATCC 12315 | N4 | − | − |
| L. helveticus | NCDO 87 | N6 | + | + |
| L. fermentum | NCDO 1750 | N7 | − | − |
| L. delbrueckii (type) | NCIB 8130 | N8 | − | − |
| L. lactis | Liebefeld 125 | N9 | − | − |
| L. acidophilus | ATCC 4356 | N12 | − | − |
| L. acidophilus | Piacenza D 179 | N16 | − | − |
| L. acidophilus | Piacenza 188 S | N17 | − | − |
| L. acidophilus | Piacenza 247 S | N18 | − | − |
| L. acidophilus | Piacenza T 145 | N21 | ± | ± |
| L. acidophilus | Piacenza T 145, 125 | N22 | ± | ± |
| L. plantarum | ATCC 8041 | N24 | − | − |
| L. buchneri | ATCC 4005 | N25 | − | − |

TABLE I-continued

| Species | Bacterial strains Source | Strain[a] | sLH1[b] | sLH2[b] |
|---|---|---|---|---|
| L. brevis | ATCC 14869 | N26 | − | − |
| L. casei (type) | ATCC 393 | N27 | − | − |
| L. helveticus | ATCC 7994 | N47 | + | + |
| L. helveticus | ATCC 7995 | N48 | + | + |
| L. helveticus | ATCC 12278 | N50 | + | + |
| L. helveticus | ATCC 13866 | N51 | + | + |
| L. bulgaricus | NCDO 1006 | N52 | − | − |
| L. bulgaricus | NCDO 1373 | N54 | − | − |
| L. lactis | NCDO 270 | N62 | − | − |
| L. lactis | NCDO 297 | N64 | − | − |
| L. bulgaricus | NCDO B 15 | N95 | − | − |
| L. bulgaricus | NCDO B 19 | N96 | − | − |
| L. bulgaricus | NCDO B 24 | N99 | − | − |
| L. helveticus | NCDO 2395 | N106 | + | + |
| L. helveticus | ATCC 11977 | N122 | + | + |
| L. bulgaricus (type) | NCDO 1489 | N123 | − | − |
| L. bulgaricus | ATCC 21815 | N124 | − | − |
| L. helveticus | ATCC 27558 | N125 | + | + |
| L. helveticus | ATCC 33409 | N126 | + | + |
| L. bulgaricus | Piacenza CO 13 | N139 | − | − |
| L. bulgaricus | Piacenza CO 14 | N141 | − | − |
| L. plantarum | ATCC 14917 | N186 | − | − |
| L. delbrueckii | ATCC 9649 | N187 | − | − |
| L. maltaromicus | ATCC 27865 | N207 | − | − |
| L. reuteri (type) | DSM 20016 | N211 | − | − |
| L. helveticus | Piacenza b 50 | N213 | + | + |
| L. helveticus | Zfirich S 400 | N217 | + | + |
| L. helveticus | our collection | N222 | + | + |
| L. helveticus | NCDO H 1 | N254 | + | + |
| L. helveticus | NCDO H 2 | N255 | + | + |
| L. helveticus | NCDO H 3 | N256 | + | + |
| L. helveticus | NCDO H 6 | N257 | + | + |
| L. helveticus | NCDO H 9 | N258 | + | + |
| L. helveticus | NCDO H 10 | N259 | + | + |
| L. helveticus | NCDO H 11 | N260 | + | + |
| L. helveticus | NCDO H 13 | N261 | + | + |
| L. helveticus | NCDO H 16 | N262 | + | + |
| L. helveticus | NCDO H 17 | N263 | + | + |
| L. helveticus | NCDO H 18 | N264 | + | + |
| L. helveticus | NCDO H 19 | N265 | + | + |
| L. helveticus | NCDO J 3 | N266 | + | + |
| L. helveticus | NCDO J 4 | N267 | + | + |
| L. helveticus | NCDO J 5 | N268 | + | + |
| L. helveticus | NCDO J 6 | N269 | + | + |
| L. helveticus | NCDO J 11 | N270 | + | + |
| L. helveticus | NCDO J 14 | N271 | + | + |
| L. helveticus | NCDO J 15 | N272 | + | + |
| L. helveticus | NCDO J 17 | N273 | + | + |
| L. helveticus | NCDO J 18 | N274 | + | + |
| L. helveticus | NCDO J 19 | N275 | + | + |
| propionibacterium freudenreichii | our collection | PP21 | − | − |
| propionibacterium shermanii | our collection | PP13 | − | − |
| Lactococcus therm. | our collection | ST1 | − | − |
| Lactococcus lactis | our collection | SL9 | − | − |
| E. coli | our collection | HB101 | − | − |

[a] Code of the Nestlé Research Centre
[b] Probe used for dotblot hybridisation:
(+) indicates hybridisation;
(−) no hybridisation

We claim:
1. An isolated sLH1 DNA fragment.
2. A fragment according to claim 1 which is detectably labelled.
3. A fragment according to claim 1 which is labelled with $^{32}P$.
4. An isolated sLH2 DNA fragment.
5. A fragment according to claim 4 which is detectably labelled.
6. A fragment according to claim 4 which is labelled with $^{32}P$.
7. A plasmid consisting of the fragment sLH1 ligated into the unique HindIII site of plasmid pACYC184.
8. A plasmid consisting of the fragment sLH2 ligated into the unique HindIII site of plasmid pACYC184.

* * * * *